United States Patent [19]

Berman

[11] Patent Number: 4,979,947
[45] Date of Patent: Dec. 25, 1990

[54] ENCAPSULATED EXPANDIBLE CONTINENCE DEVICE

[76] Inventor: Irwin R. Berman, 2301 Parkwood Dr., Brunswick, Ga. 31520

[21] Appl. No.: 786,116

[22] Filed: Oct. 10, 1985

[51] Int. Cl.⁵ .............................................. A61F 13/15
[52] U.S. Cl. ................................................... 604/369
[58] Field of Search ......................... 604/364, 285–287, 604/15, 1 R, 353, 377, 329–332, 355, 55, 381, 904, 369; 128/435, 325, 341–344

[56] References Cited

U.S. PATENT DOCUMENTS

| | | | |
|---|---|---|---|
| 1,561,020 | 11/1925 | Pond | 604/287 |
| 1,887,526 | 11/1932 | Spielberg et al. | 604/287 |
| 2,243,529 | 5/1941 | Grossman et al. | |
| 2,386,590 | 10/1945 | Calhoun | 604/15 |
| 2,508,690 | 5/1950 | Schmerl | |
| 2,701,559 | 2/1955 | Cooper | |
| 2,773,502 | 12/1956 | Kaslow et al. | |
| 2,839,049 | 6/1958 | MacLean | |
| 2,884,925 | 5/1959 | Meynier, Jr. | 604/286 |
| 2,927,584 | 3/1960 | Wallace | |
| 2,931,353 | 4/1960 | Kitzul | 128/1 R |
| 2,962,023 | 11/1960 | Chappaz | 604/285 |
| 3,155,097 | 11/1964 | Barron | |
| 3,189,031 | 6/1965 | Andersen | |
| 3,528,429 | 9/1970 | Beal et al. | |
| 3,635,223 | 1/1972 | Klieman | |
| 3,664,328 | 5/1972 | Moyle, Jr. et al. | |
| 3,688,763 | 9/1972 | Cromarty | |
| 3,739,750 | 6/1973 | Shinjo | |
| 3,766,924 | 10/1973 | Pidgeon | |
| 3,780,730 | 12/1973 | Weisman | |
| 3,881,485 | 5/1975 | Davis, Jr. | 604/286 |
| 3,916,898 | 11/1975 | Robinson | 604/286 |
| 3,958,556 | 5/1976 | Schenk | 128/1 R |
| 3,995,636 | 12/1976 | Murray et al. | |
| 4,034,754 | 7/1977 | Haerr | |
| 4,077,409 | 3/1978 | Murray | 604/286 |
| 4,209,009 | 6/1980 | Hennig | 128/1 R |
| 4,237,893 | 12/1980 | Michaels | |
| 4,258,704 | 3/1981 | Hill | |
| 4,306,563 | 12/1981 | Iwatschenko | |
| 4,338,941 | 7/1982 | Payton | |
| 4,344,434 | 8/1982 | Robertson | 128/1 R |

FOREIGN PATENT DOCUMENTS

| | | |
|---|---|---|
| 188376 | 7/1986 | European Pat. Off. |
| 2754807 | 6/1979 | Fed. Rep. of Germany ...... 604/338 |
| 788407 | 1/1958 | United Kingdom |
| 2153686 | 8/1985 | United Kingdom |

*Primary Examiner*—Jerome Kruter
*Attorney, Agent, or Firm*—Fleit, Jacobson, Cohn, Price, Holman & Stern

[57] ABSTRACT

A continence device in the form of a cube or block of resilient foam material capable of being collapsed into a small volume condition and encapsulated in a capsule of gelatin or the like and which includes a string or cord passing through the material and connected with a traction bead engaged with a distal surface of the block or cube or foam material. The continence device provides for voluntary trapping or blockage of gastrointestinal effluent when voluntary and natural control is lacking such as when a person has had a colostomy, ileostomy, or in other situations involving fecal incontinence. A introducer is provided for inserting the capsule, the reduced volume soft foam material therein and the line or cord and traction bead into a body orifice such as a stomal orifice, anus of the like. The introducer is in the form of a tubular member, such as a straw which is passed over the cord or string and has one end engaged with the capsule and is provided with a flexible section to facilitate insertion of the device into the desired body orifice with the gelatin capsule then being dissolved in the presence of body warmth and moisture to enable the compressed soft foam material to expand to a predetermined size and shape for blockage and temporary retention of gastrointestinal content in the body orifice. Traction on the string or cord during withdrawal results in compression of the contained foam cube by means of the traction bead facilitating comfortable withdrawal of the continence device from the body orifice.

10 Claims, 1 Drawing Sheet

U.S. Patent  Dec. 25, 1990  4,979,947
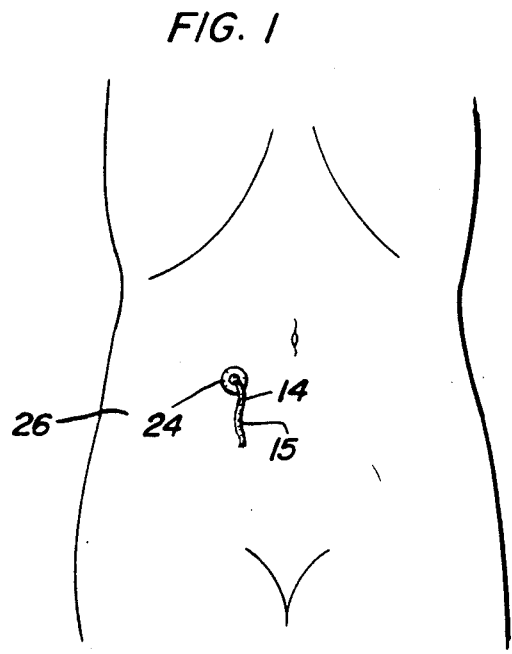
FIG. 1
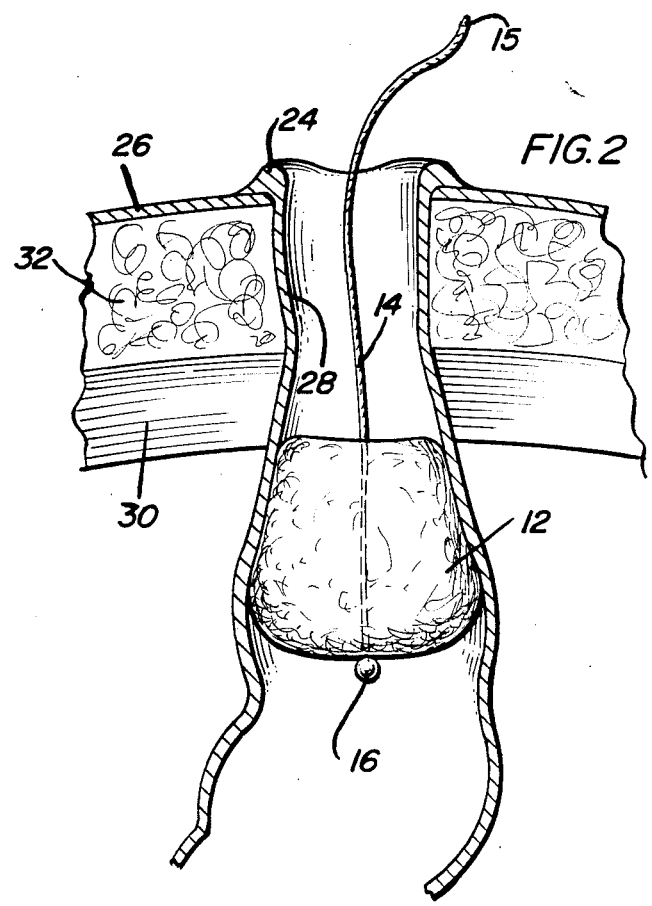
FIG. 2
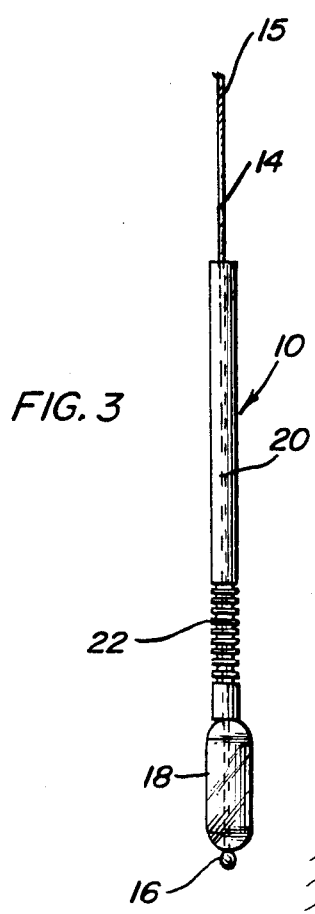
FIG. 3
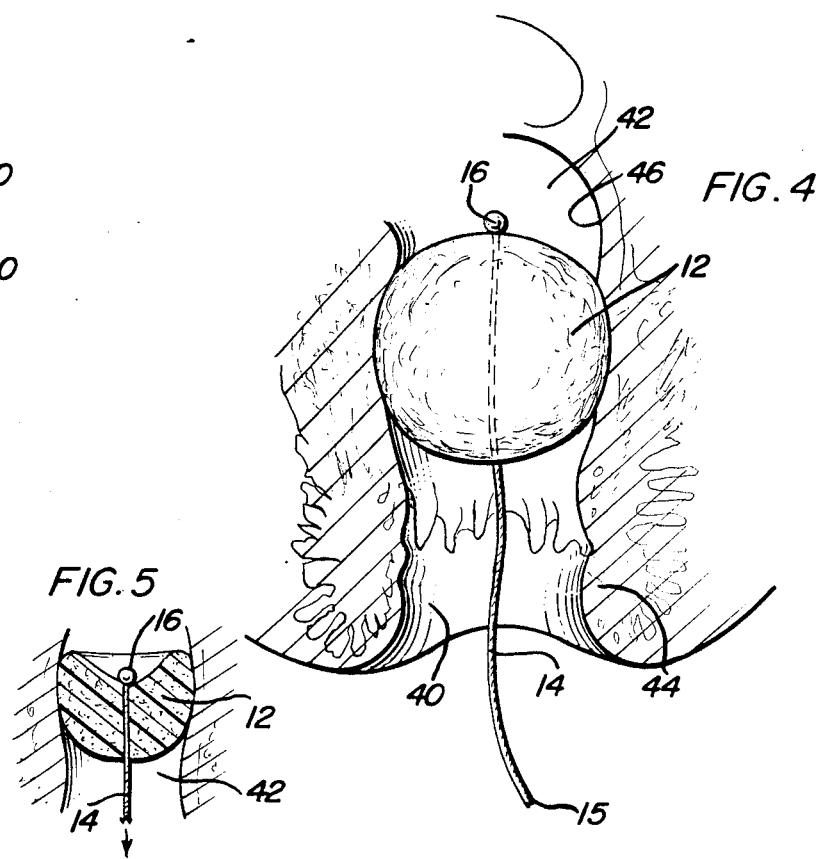
FIG. 4
FIG. 5

ENCAPSULATED EXPANDIBLE CONTINENCE DEVICE

BACKGROUND OF THE INVENTION

1. Field of the Invention

A continence device in the form of a cube or block of resilient foam material capable of being collapsed into a small volume condition and encapsulated in a capsule of gelatin or the like and which includes a string or cord passing through the material and connected with a traction bead engaged with a distal surface of the block or cube of foam material. The continence device provides for voluntary trapping or blockage of gastrointestinal effluent when voluntary and natural control is lacking such as when a person has had a colostomy, ileostomy, or in other situations involving fecal incontinence. An introducer is provided for inserting the capsule, the reduced volume soft foam material therein and the line or cord and traction bead into a body orifice such as a stomal orifice, anus or the like. The introducer is in the form of a tubular member, such as a straw which is passed over the cord or string and has one end engaged with the capsule and is provided with a flexible section to facilitate insertion of the device into the desired body orifice with the gelatin capsule then being dissolved in the presence of body warmth and moisture to enable the compressed soft foam material to expand to a predetermined size and shape for blockage and temporary retention of gastrointestinal content in the body orifice.

2. Information Disclosure Statement

Various devices are known which can be inserted into a body orifice while in a reduced volume condition, permitted to expand and then retracted. Such devices include inflatable hollow resilient members and other expandable members for use in obtaining specimen material for diagnostic procedures, absorption of body fluids such as catamenial devices and the like. Also, it is known to provide collection bags for receiving body fluids and effluent which are involuntarily discharged by persons that are incapable of controlling the discharge of gastrointestinal effluent for various reasons.

SUMMARY OF THE INVENTION

An object of the present invention is to provide a continence device in the form of an encapsulated and expandable block or cube of soft, resilient foam material that is compressed into a small volume condition and received in a capsule of gelatin or similar material which facilitates intubation of the device into a body orifice, hollow organ or the like with body warmth and moisture dissolving the capsule for expansion into a predetermined shape and size to provide voluntary trapping or blockage of organ effluent when voluntary natural control of discharge of such effluent is lacking.

Another object of the invention is to provide a continence device in accordance with the preceding object in which the block or cube of foam material is provided with a flexible cord or string passing therethrough and being of the length to be accessible from the exterior of the body orifice in which the device is positioned to enable retrieval and removal of the expanded block or cube in which the cord includes a traction bead on the end thereof engaged with the surface of the block or cube opposite from the free end of the cord to provide a traction bead to afford compression of the foam material during withdrawal and to assure that the cord or string will remain attached to the block or cube of foam material when it is being removed from the body orifice or cavity.

A further object of the invention is to provide a continence device in accordance with the preceding objects together with an introducer in the form of a hollow rod, tube or straw through which the flexible cord or string is passed with one end of the straw engaging the capsule to enable the capsule to be guided and manipulated during intubation of the capsule into the body orifice with the straw including a flexible section to enable the capsule to follow curves or contours encountered during intubation with the straw being removed after the capsule has been accurately positioned in the desired location.

Still another object of the invention is to provide a continence device which may be efficiently inserted into a skin level ileostomy or colostomy to effect temporary blockage of the ileostomy or colostomy until such time as the user wishes to disengage the blockage and empty the retained gastrointestinal contents into a suitable container, bag, commode or other disposal point thereby enabling the permanent customary ileostomy or colostomy bag with its attendant hazards of weight, volume and odor being avoided.

A still further object of the invention is to provide a continence device for efficient and effective use by a person having anal incontinence including loss or absence of voluntary control of defecation in which the device is inserted into the anal canal and allowed to expand for temporary blockage and then withdrawn as desired to permit release of gastrointestinal content retained into a suitable container, commode or the like.

Still further objects of the invention may be to accomplish similar voluntary control of drainage in other hollow organs such as devices for control of vaginal and nasal hemorrhage.

These together with other objects, applications and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWING

FIG. 1 is a schematic illustration of a user having a surgically performed ileostomy in which the continence device of the present invention is used.

FIG. 2 is a sectional view, on an enlarged scale, illustrating the present invention in use for forming a temporary blockage in the stoma through the abdominal wall.

FIG. 3 is an elevational view of the continence device of the present invention illustrating the introducer associated with the capsule, string or cord and traction bead.

FIG. 4 is a sectional view illustrating the continence device of the present invention in anorectal use.

FIG. 5 is a schematic illustration showing the manner in which the traction bead and cord can produce compression and exert removal force on the expanded block or cube of soft foam material.

DESCRIPTION OF THE PREFERRED EMBODIMENTS

Referring now specifically to the drawings, the continence device of the present invention is generally designated by numeral 10 and includes a block or cube of expandable, resilient, soft foam plastic material 12 which, in its fully expanded shape may be cubical or other predetermined shapes having predetermined expanded size depending upon use of the device. A tension cord or string 14 is connected to the block or cube of foam material 12 by passing therethrough and having a traction bead 16 connected thereto which will engage the surface of the block or cube of foam material 12 in remote relation to the free end 15 of the cord or string 14 so that the block or cube of foam material 12 can be removed by exerting tension force on the cord or string which will move the central portion of the block or cube 12 along with the string while the peripheral portion thereof may lag behind slightly thereby effectively reducing the cross-sectional configuration of the block or cube of foam material 12 when it is being removed from a body orifice or cavity as discussed in more detail hereinafter.

The block or cube of foam material 12 is compressed and encapsulated in a capsule 18 of gelatin or similar material capable of being dissolved by body warmth and moisture. As illustrated in FIG. 3, the capsule is elongated and generally cylindrical in cross-sectional configuration with the traction bead 16 oriented at one end thereof and externally of the capsule. Thus, the continence device 10, when it is ready to be intubated into a body orifice or cavity consists of the compressed or collapsed foam material 12 encapsulated in the capsule 18 and provided with the cord or string 14 extending therethrough with a traction bead 16 on the distal end thereof. To facilitate intubation into a body orifice or cavity, an introducer 20 is provided which is in the form of a hollow tube or rod preferably in the form of a sipping straw of the type which has an accordion, concertina or a bellows type flexible section 22 incorporated into the straw adjacent one end thereof with the end of the straw adjacent the flexible section 22 engaging the end of the capsule 18 remote from the traction bead 16 when the straw 20 is inserted over the cord or string 14 which may be a nylon cord or string or other similar material. Thus, by inserting the straw or introducer 20 over the cord or string 14 and tensioning the cord or string 14 slightly, the capsule 18 may be easily inserted into a body orifice or cavity with the flexible section enabling the introducer to be initially curved or curved during insertion to enable the capsule to follow or move around areas of curvature as may become necessary when positioning the capsule 18 and the compressed block or cube of foam material 12 in the desired position in the body cavity or orifice.

FIGS. 1 and 2 illustrate the continence device 10 of the present invention inserted into a stomal orifice in the form of a surgically performed ileostomy in which the outer end portion 24 of the bowel or conduit 28 projects above the skin surface 26 with the conduit 28 extending through the abdominal wall 30 and the subcutaneous material 32 and sutured to the skin 26 in a conventional and well known manner. As illustrated, the capsule is inserted into the conduit 28 and positioned inwardly of the abdominal wall so that when the capsule dissolves, the compressed block or cube of foam material 12 may expand closely adjacent the inner surface of the abdominal wall 30 as illustrated in FIG. 2 thus forming a temporary blockage or obturation the conduit 28. The use of the soft foam obturation avoids the hazards of pressure necrosis of the surrounding intestines such as may occur when more rigid or semi-rigid devices are used such as balloons since a balloon when expanded exerts relatively high pressure over a smaller area of contact. The soft foam material has some degree of porosity but is substantially non-absorbant so that it will effectively block passage of liquids and solids for retaining them while allowing some degree of passage of flatus, gas and the like. When it is desired to remove the temporary blockage to discharge or empty the retained contents into a collection bag, commode or the like, it is only necessary for the wearer to grasp the free end 15 of the cord or string 14 and pull outwardly in a gentle manner with such tension causing the block or cube of foam material 12 to somewhat reduce in cross-sectional configuration as illustrated in FIG. 5 so that it can be effectively, comfortably and painlessly removed without injury to surrounding tissue thereby providing voluntary trapping or blockage of gastrointestinal effluent where natural control is lacking and yet enable the user to easily empty the retained material when desired. While FIGS. 1 and 2 illustrate the device associated with an ileostomy, it also can be used just as effectively in connection with a surgically performed colostomy.

In addition, it may be inserted into the anal canal as illustrated in FIG. 4 in which the block or cube of foam material 12 has been inserted into the anus 40 and into the rectum 42 past the sphincter muscle area 44 and into engagement with the rectal wall 46 as illustrated in FIG. 4. Thus, a user who has lost natural control of the sphincter muscles and other natural continence controls, may insert the continence device 10 so that when the block or cube of foam material 12 expands, it will expand into the anal canal for blockage and when desired, it can be withdrawn to permit release of gastrointestinal content into a commode or the like thereby enabling the user who has lost voluntary control of defecation to again obtain voluntary control of defecation by selecting at what point in time the continence device 10 is to be removed from the anal canal. The construction of the block or cube of foam material 12, the cord or string 14 and the traction bead 16 is such that when tension force is exerted on the cord 14 during removal of the block or cube of foam material 12, the force exerted on the distal surface of the block or cube will allow inward deflection or compression and reduction in overall size of the foam block or cube thereby facilitating extraction through the anus thereby greatly facilitating voluntary removal of the temporary blockage for emptying the gastrointestinal content that has been retained without discomfort, pain or injury to the tissue surfaces engaged by the expanded block or cube of soft foam material. While the continence device of this invention has been disclosed in use for voluntary trapping and blockage of gastrointestinal effluent, it can be used for various similar uses such as a catamenial device or in any area where it is desired to trap or block flow in a body orifice such as to control a vaginal or nasal hemorrhage so that the user can voluntarily remove the device for discharge of the retained material whenever desired. Also, the soft foam plastic material enables easy impregnation of a deodorant charcoal or other additives that may be desirable during use.

The foregoing is considered as illustrative only of the principles of the invention. Further, since numerous modifications and changes will readily occur to those skilled in the art, it is not desired to limit the invention to the exact construction and operation shown and described, or to the organs and structures herein named and accordingly, all suitable modifications and equivalents may be resorted to, falling within the scope of the invention.

I claim:

1. A continence device for guided insertion into a body orifice for temporary blocking of the orifice comprising a body of soft, resilient, expandable and compressible foam material, a flexible cord attached to said body and a capsule encapsulating the body of foam material and retaining it in a compressed small volume condition for insertion into the body orifice, said capsule being constructed of material dissolved by body warmth and moisture to enable the foam material to expand from compressed condition to a predetermined larger size and shape for effectively and temporarily blocking the body orifice, said cord being accessible from externally of the body to enable tension to be exerted thereon to reduce the size of the body of foam material to reduce injury during extraction for removing the body of material to enable the user to voluntarily empty retained material from the body orifice, said foam material being substantially non-absorbent for effectively blocking passage of solids and liquids while allowing passage of flatus to some degree.

2. The device as defined in claim 1 wherein said cord extends through the body of foam material, and a traction bead on the terminal end of the cord which engages the foam material to prevent the cord from pulling through the foam material and to reduce the size of the body of foam material by compression during withdrawal of the device.

3. The device as defined in claim 1 together with an introducer for intubating the capsule into a body orifice, said introducer comprising a tubular straw through which the cord is inserted with one end of the straw engaging the capsule so that the cord, straw and capsule are retained in assembled relation by exerting a slight tension on the cord and holding the straw against the capsule.

4. The device as defined in claim 3 wherein said straw includes a flexible section adjacent the end thereof engaged with the capsule to enable the capsule to follow curves or contours encountered during intubation into the body orifice.

5. The device as defined in claim 4 wherein said cord extends through the body of material, and a traction bead on the terminal end of the cord which engages the foam material to prevent the cord from pulling from the foam material and to reduce the size of the body of foam material by compression during withdrawal of the device, said bead having a cross-sectional area substantially less than the cross-sectional area of the expanded body of foam material whereby tension on the cord during removal of the body of foam material will cause the central portion of the foam material to move while the peripheral portion of the foam material is frictionally retained by contact with the interior of the body orifice thereby reducing the cross-sectional area of the body of foam material so that it can be removed from the orifice without injury to surrounding tissues.

6. A device as defined in claim 4 wherein the expanded dimensions of the body of foam material form a blockage of a bowel immediately inwardly of the abdominal wall of a user having a surgically performed ileostomy or colostomy until the user voluntarily removes the continence device for emptying the retained effluent.

7. The device as defined in claim 4 wherein the expanded dimensions of the body of foam material effectively blocks the anal passage inwardly of the sphincter muscle area for blocking discharge of gastrointestinal effluent until the user voluntarily removes the continence device for emptying the retained effluent.

8. An encapsulated expansion device for insertion into a body orifice for temporary blockage of the orifice comprising a body of soft, resilient, expandable and compressible foam material, said body being substantially non-absorbent for blocking liquid and solid flow in the body orifice and being pervious to gases to enable passage of flatus, a flexible cord attached to said body and a capsule completely enclosing and encapsulating the body of foam material and retaining it in a compressed small volume condition for insertion into the body orifice, said capsule being constructed of material impervious to moisture to preclude contact of moisture with the body of foam material during insertion into desired position in the body orifice, said material being dissolved by body warmth and moisture to enable the foam material to expand to a predetermined size and shape for effectively and temporarily blocking the body orifice with the cord being accessible from externally of the body to enable tension to be exerted thereon to reduce the size of the body of foam material during voluntary extraction for removing the body of material to empty retained material from the body orifice, said cord extending through the body of foam material, and an enlargement on the terminal end of the cord engaging the surface of the foam material inwardly of the body orifice to prevent the cord from pulling through the foam material when tension is exerted thereon.

9. The expansion defice as defined in claim 8 together with an elongated introducer tube inserted over the cord with one end engaging the capsule, said tube having a smaller perimeter than the capsule to retain the capsule axially aligned with the end of the tube when tension is exerted on the cord, said tube including a bellows-type flexible section adjacent the end which engages the capsule to enable the capsule to follow curves in the body orifice during insertion.

10. The expansion device as defined in claim 9 wherein said enlargement on the terminal end of the cord has a cross-sectional area substantially less than the cross-sectional area of the expanded body of foam material whereby tension on the cord during removal of the body of foam material will reduce the cross-sectional configuration of the body of foam material so that it can be effectively, comfortably and painlessly removed without injury to surrounding tissue, said introducer tube providing in-depth insertion of the capsule and compressed body of foam material without trauma with expansion of the body of foam materials providing obturation of the body orifice with passage of gas without obsorption and without use of internal retention means.

* * * * *